United States Patent

Rea et al.

[11] Patent Number: 4,474,182
[45] Date of Patent: Oct. 2, 1984

[54] SURGICAL STOMA TOOL AND METHODS OF MAKING AND USING THE SAME

[76] Inventors: Herman Rea, Rte. 2, Box 478B; Ralph E. Wehmer, Rte. 2, Box 478, both of Florissant, Mo. 63034

[21] Appl. No.: 308,101

[22] Filed: Oct. 5, 1981

[51] Int. Cl.³ .............................................. A61M 29/00
[52] U.S. Cl. ................................... 128/341; 128/303 R
[58] Field of Search .......... 128/303 R, 200.26, 207.14, 128/207.15, 207.16, 207.17, 341, 127, 343; 215/296, 15

[56] References Cited

U.S. PATENT DOCUMENTS

| 242,743 | 12/1876 | Leight | 128/152 |
|---|---|---|---|
| 1,551,499 | 8/1925 | Homan | 128/343 |
| 1,610,947 | 12/1926 | Hosmer | 128/341 |
| 1,879,307 | 9/1932 | Kennedy | 128/341 |
| 2,786,469 | 3/1957 | Cohen | 128/343 |
| 3,675,642 | 7/1972 | Lord | 128/341 |
| 3,800,791 | 4/1974 | Visor | 128/152 |

FOREIGN PATENT DOCUMENTS 233980 5/1925 United Kingdom ............... 128/341

Primary Examiner—Henry J. Recla
Assistant Examiner—Karin M. Reichle

[57] ABSTRACT

The present invention relates to a Surgical Stoma Tool and methods of making and using the same wherein an elongated circular cylindrical element which is provided at one end thereof with a spherical surface and a handle on the other end with an annular stop ring proximate the spherical surface.

2 Claims, 1 Drawing Figure

SURGICAL STOMA TOOL AND METHODS OF MAKING AND USING THE SAME

BACKGROUND OF THE INVENTION

Conventional techniques for maintaining an opening at the outlet of the human urinary tract, or stoma, following what is normally classified as a urinary diversion or bypass operation typically require the patient to visit his physician or obtain outpatient care.

The present device permits the patient under ordinary circumstances to perform the necessary manipulation to maintain the stoma in an open status without professional assistance.

SUMMARY

It is therefore an object of the present invention to provide a Surgical Stoma Tool device which includes an elongated circular, cylindrical device provided with a semi-spherical surface at one end and a handle at the other end and an annular stop disposed therebetween.

An object of the present invention is to provide such a device which is surgically clean and may be maintained in such condition and the surface of which may be maintained smooth and sanitary.

A further object of the present invention is to provide such a device which is simply and economically manufactured and used.

These together with other objects and advantages which will become subsequently apparent, reside in the details and construction and operation as more fully hereinafter described and claimed, reference being had to the accompanying drawings forming a part hereof, wherein like numerals refer to like parts throughout, and in which;

DETAILED DESCRIPTION OF THE INVENTION

Figure 1:
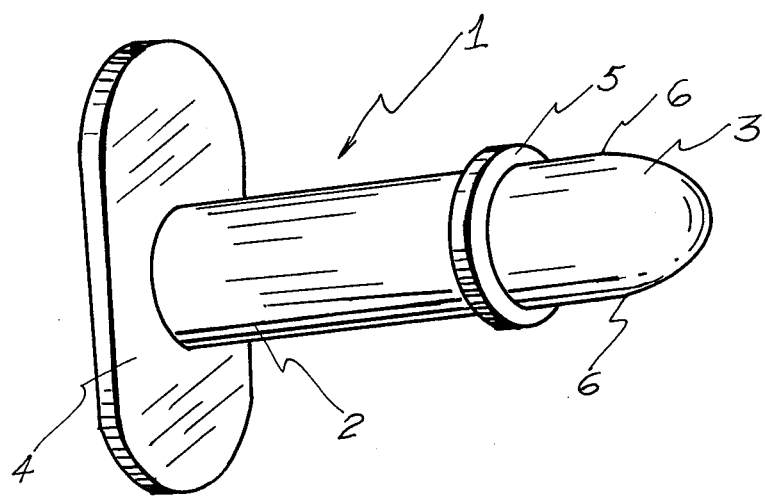
FIG. 1 is a perspective view of a Surgical Stoma Tool device constructed in accordance with and embodying the present invention.

Referring now in more detail and by reference characters to the drawings which illustrate practical embodiments of the present invention, FIG. 1, is a perspective view of a Surgical Stoma Tool device, 1, constructed in accordance with, used in and embodying the present invention.

As shown in FIG. 1, surgical stoma tool device, 1, comprises an elongated, circular cylindrical element, 2, provided with a semi-spherical surface, 3, at one end thereof and handle means, 4, at the other end, with stop ring, 5, mounted on element, 2, and disposed between end, 3, and handle means, 4.

In the preferred embodiment of the invention the parts will be constructed of stainless steel or other suitable sanitary material and element, 2, will be solid or weighted in order to assist the manipulation. Further, the surface, 6, of element, 2, will preferably be polish finish particularly at the semi-spherical end, 3.

It should be understood that changes and modifications in the form, construction, arrangement, and combination of the surgical stoma tool device and methods of making and using the same may be made and substituted for those herein shown and described without departing from the nature and principle of my invention.

Having thus described my invention, what I claim is new and desire to secure by U.S. Letters Patent is:

1. A surgical stoma tool comprising, an elongated, straight, solid and rigid circular cylindrical element of constant diameter provided with a first and second end thereof, and said element provided with a closed semi-spherical surface at the first end, the surface thereof polish finished, and handle means operably mounted proximate the second end of said element, comprising a flat plate mounted at right angles to the elongated member, and a single annular stop means operably mounted on said element and disposed between said first and second ends, proximate said first end and at a distance therefrom reflecting the desired depth of insertion, said annular stop means comprising an annular ring.

2. A surgical stoma tool as described in claim 1 wherein said elongated element is weighted.

* * * * *